(12) United States Patent
Kehtarnavaz et al.

(10) Patent No.: US 9,364,669 B2
(45) Date of Patent: Jun. 14, 2016

(54) AUTOMATED METHOD OF CLASSIFYING AND SUPPRESSING NOISE IN HEARING DEVICES

(75) Inventors: Nasser Kehtarnavaz, Plano, TX (US); Vanishree Bijadi Gopalakrishna, Redmond, WA (US); Philipos C. Loizou, Plano, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/358,377

(22) Filed: Jan. 25, 2012

(65) Prior Publication Data
US 2013/0022223 A1  Jan. 24, 2013

Related U.S. Application Data

(60) Provisional application No. 61/435,934, filed on Jan. 25, 2011.

(51) Int. Cl.
| H04R 25/00 | (2006.01) |
| A61N 1/36 | (2006.01) |
| A61N 1/05 | (2006.01) |

(52) U.S. Cl.
CPC .......... *A61N 1/36032* (2013.01); *A61N 1/0541* (2013.01); *H04R 25/554* (2013.01); *H04R 25/558* (2013.01); *H04R 2225/51* (2013.01); *H04R 2225/67* (2013.01)

(58) Field of Classification Search
CPC ............. A61N 1/36032; A61N 1/0541; H04R 25/554; H04R 2225/41; H04R 2225/67; H04R 25/558

USPC .................... 381/314–315, 317; 607/57, 137
See application file for complete search history.

(56) References Cited

U.S. PATENT DOCUMENTS

| 5,101,665 | A | * | 4/1992 | Mizuno | 73/721 |
| 5,545,912 | A | * | 8/1996 | Ristic et al. | 257/417 |
| 6,035,050 | A | * | 3/2000 | Weinfurtner et al. | 381/313 |
| 6,324,907 | B1 | * | 12/2001 | Halteren et al. | 73/431 |
| 6,781,231 | B2 | * | 8/2004 | Minervini | 257/704 |
| 7,319,769 | B2 | * | 1/2008 | Allegro-Baumann et al. | 381/312 |
| 7,599,507 | B2 | * | 10/2009 | Hansen | 381/317 |
| 7,715,576 | B2 | * | 5/2010 | Ribic | 381/312 |
| 7,808,060 | B2 | * | 10/2010 | Hsiao | 257/416 |
| 7,957,548 | B2 | * | 6/2011 | Meier et al. | 381/312 |
| 2006/0034472 | A1 | * | 2/2006 | Bazarjani et al. | 381/111 |
| 2008/0130935 | A1 | * | 6/2008 | Sato et al. | 381/361 |
| 2008/0219482 | A1 | * | 9/2008 | Sato | 381/174 |
| 2011/0051963 | A1 | * | 3/2011 | Barthel et al. | 381/314 |
| 2011/0115064 | A1 | * | 5/2011 | Radojcic et al. | 257/686 |
| 2011/0293126 | A1 | * | 12/2011 | Maekawa et al. | 381/355 |

* cited by examiner

Primary Examiner — Curtis Kuntz
Assistant Examiner — Ryan Robinson
(74) Attorney, Agent, or Firm — Winstead PC

(57) ABSTRACT

The claimed invention is directed to a real-time noise classification and tuning system for cochlear implant and other hearing device applications. The system is capable of automatically selecting the optimized parameters of a noise suppression algorithm in response to different noisy environments. The feature vector and the classifier deployed in the system to automatically identify the background noise environment are selected so that the computation burden is kept low to achieve a real-time throughput. The results reported herein indicate improvement in speech enhancement when using this intelligent real-time hearing device system.

6 Claims, 5 Drawing Sheets

BLOCK DIAGRAM OF THE PROPOSED NOISE-ADAPTIVE COCHLEAR IMPLANT SYSTEM

BLOCK DIAGRAM OF THE PROPOSED NOISE-ADAPTIVE COCHLEAR IMPLANT SYSTEM

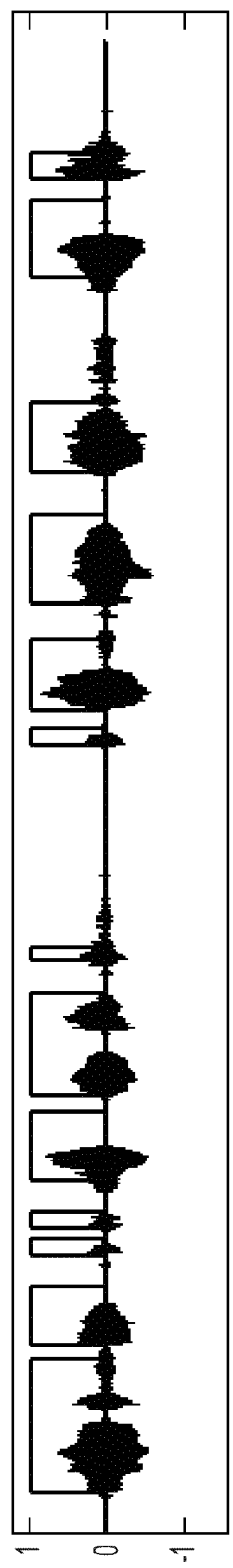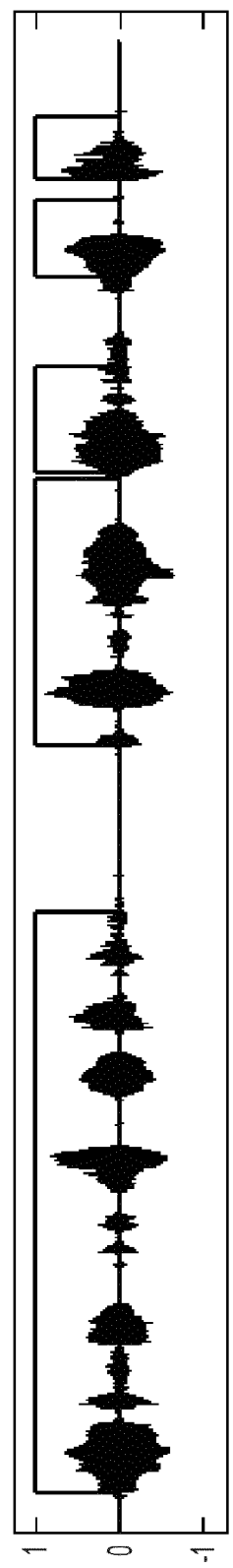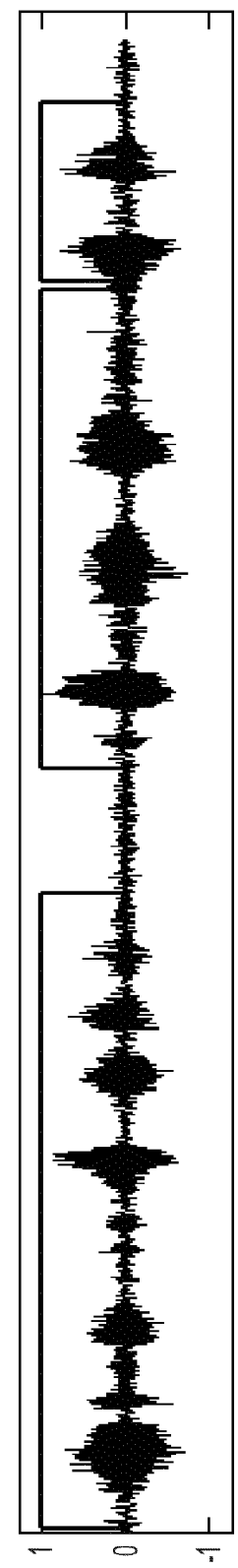

AUTOMATED METHOD OF CLASSIFYING AND SUPPRESSING NOISE IN HEARING DEVICES

STATEMENT REGARDING FEDERALLY-SPONSORED RESEARCH OR DEVELOPMENT

This invention was made with government support under Grant No. R01 DC010494 awarded by the National Institute of Deafness and Other Communications Disorders, National Institutes of Health. The government has certain rights in the invention.

CROSS-REFERENCES TO RELATED APPLICATIONS

This Application claims the benefit under 35 U.S.C. §119 (e) of U.S. Provisional Patent Application Set. No. 61/435, 934 filed Jan. 25, 2011, which is incorporated herein by reference in its entirety as if fully set forth herein.

FIELD OF THE INVENTION

The invention relates to a hearing device and a method of operation, and in particular, but not exclusively, for noise suppression in a cochlear implant or hearing aid.

BACKGROUND OF THE INVENTION

More than 118,000 people around the world have received cochlear implants (CIs). Since the introduction of CIs in 1984, their performance in terms of speech intelligibility has considerably improved. However, their performance in noisy environments still remains a challenge. The speech understanding rate by CI patients is reported to be high in quiet environments but is shown to greatly diminish in noisy environments. Several speech enhancement algorithms, are proposed in the literature to address the performance aspect in noisy environments. However, no strategy has been offered in the literature to automatically tune these algorithms in order to obtain improved performance across different kinds of background noise environments encountered in daily lives of CI patients.

Enhancement or noise suppression algorithms are known in the prior art which provide improved performance for a number of noisy environments. The claimed invention is directed to an automatic mechanism to identify the noise environment and tune or adjust the noise suppression component to different noisy environments in a computationally efficient or real-time manner. The motivation here has been to improve performance of CIs by allowing them to automatically adapt to different noisy environments. The real-time requirement is the key aspect of the developed solution as any computationally intensive approach is not practically useable noting that the processors that are often used in CIs are of limited computational power.

More specifically, a real-time CI system is developed herein which automatically classifies 10 commonly encountered noisy environments in order to switch among the noise suppression parameters that are optimized for these environments. The classification is done in such a way that little additional computation burden is added to the CI speech processing pipeline. Depending on the outcome of the noise classification, the system automatically and on-the-fly switches to those parameters which provide optimum performance for that particular noisy environment. Although the claimed invention is discussed with respect to cochlear implants, it should be noted that the invention has applicability in a variety of hearing devices including hearing aids and Bluetooth devices.

SUMMARY OF THE INVENTION

The claimed invention is a noise adaptive CI system that is capable of detecting the change in the background noise on its own without any user intervention. As a result, optimized noise suppression parameters are automatically switched to that background noise.

The invention may allow an improved user experience and/or may allow improved adaptation of an audio signal to the audio environment. In particular, the invention may allow an improved adaptation to of an audio signal with respect to the environment. For example, audio perception characteristics may be considerably different in different noise scenarios and the hearing device according to the invention may allow such noise dependency to be determined and automatically taken into account when adapting the audio processing to the user.

An embodiment of the claimed invention is directed to a real-time noise classification and tuning system for cochlear implant applications. The system is capable of automatically selecting the optimized parameters of a noise suppression algorithm in response to different noisy environments. The feature vector and the classifier deployed in the system to automatically identify the background noise environment are selected so that the computation burden is kept low to achieve a real-time throughput. The results reported herein indicate improvement in speech enhancement when using this intelligent real-time cochlear implant system.

BRIEF DESCRIPTION OF THE DRAWINGS

Embodiments of the invention will be described, by way of example only, with reference to the drawings, in which

FIG. 2a illustrates noise detector output of clean speech signal without guard time correction; FIG. 2b illustrates VAD output of clean speech signal with guard time correction; and FIG. 2c illustrates VAD output of corrupted speech signal by car noise at 5 dB with guard time correction, in accordance with some embodiments of the invention;

DETAILED DESCRIPTION OF EXEMPLARY EMBODIMENTS

An embodiment of the invention is directed to a hearing device system comprising a hearing device and a control device, the control device comprising: a signal interface that is adapted to receive data representing the acoustic environment external to the ear, and transmit an optimal algorithm to the hearing device; and a module for analyzing the data representing the acoustic environment external to the ear, and calculating the optimal algorithm for digital signal processing, the control device being operable to be responsive to the acoustic environment data transmitted thereto to automatically derive the optimal algorithm based upon the data and to transmit the optimal algorithm to the hearing device; wherein the hearing device is adapted to receive the optimal algorithm transmitted thereto by the control device and to perform speech enhancement in real time using the received optimal algorithm.

In an embodiment of the invention, the hearing device system further comprises a computer in communication with the control device for at least one of signal analysis, algorithm processing, and audiometric examination. In certain embodiments of the invention, the hearing device system is implemented on a smartphone platform.

A further embodiment of the invention is directed to a method of operating a hearing device, the method comprising: providing a hearing device and a control device, the control device comprising a signal interface that is adapted to receive data representing the acoustic environment external to the ear, and transmit an optimal algorithm to the hearing device; and a module for analyzing the data representing the acoustic environment external to the ear, and calculating the optimal algorithm for digital signal processing, the control device being operable to be responsive to the acoustic environment data transmitted thereto to automatically derive the optimal algorithm based upon the data and to transmit the optimal algorithm to the hearing device; wherein the hearing device is adapted to receive the optimal algorithm transmitted thereto by the control device and to perform speech enhancement in real time using the received optimal algorithm; the method further comprising the steps of: adjusting the hearing device in an audiometric process to adapt the hearing device to the hearing loss of the user; deriving data representing the acoustic environment external to the ear; transmitting the data representing the acoustic environment external to the ear to the control device; analyzing the data representing the acoustic environment external to the ear and automatically calculating the optimal algorithm for performing speech enhancement; transmitting the optimal algorithm to the hearing device; and performing speech enhancement using the received optimal algorithm.

Figure 1:
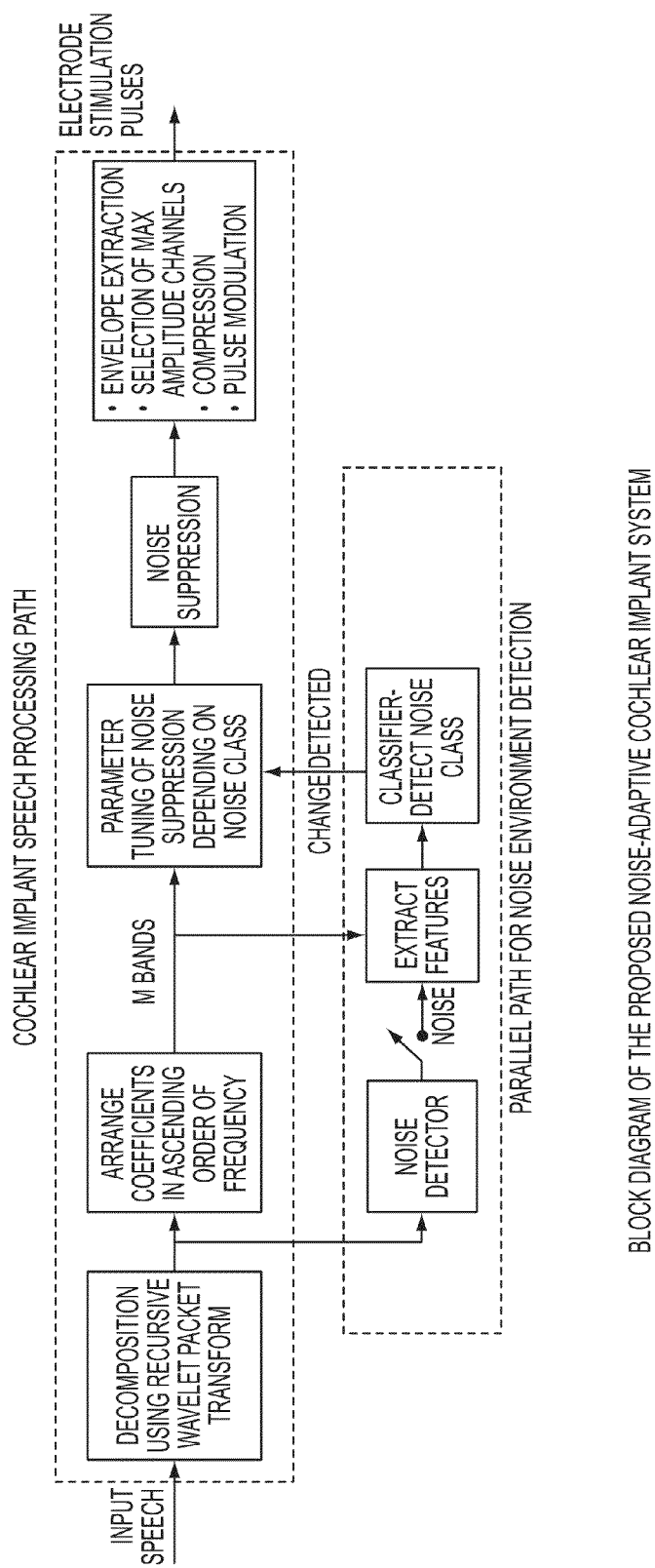
FIG. 1 illustrates a block diagram of the intelligent cochlear implant system of the invention.

A block diagram of the developed intelligent system is set forth in FIG. 1. First, the input speech signal is windowed and decomposed into different frequency bands. Most commercial CIs use a bandpass filterbank or FFT to achieve this decomposition. Based on the previously developed noise suppression algorithms, the effect of noise is suppressed by appropriately weighting the magnitude spectrum. From the weighted magnitude spectrum, channel envelopes are extracted by combining the wavelet packet coefficients of the bands which fall in the frequency range of a particular channel. The envelopes are then passed through a rectifier and lowpass filtered. Finally, they are compressed using a logarithmic compression map. Based on these compressed channel envelopes, the amplitude of stimulating pulses for CI implanted electrodes are determined.

In a parallel path, the first stage of the wavelet packet transform (WPT) coefficients of the windowed signal are used to detect if a current window is voiced/unvoiced speech or noise via a voice activity detector (VAD). If the input windowed signal is found to be noise, signal features are extracted using the wavelet packet coefficients that are already computed for the CI speech processing pipeline. The extracted feature vector is fed into a Gaussian Mixture Model (GMM) classifier to identify the background noise environment. Then, the system switches to those parameters that are optimized for that environment.

According to the hearing aid studies that have been done, it is known that on average, hearing aid patients spend around 25% of their time in quiet environments while the remaining 75% of their time is distributed among speech, speech in noise and noisy environments. Different background noise environments encountered in daily lives of patients depends on many demographic factors such as age, life style, living place, working place, etc. Hearing aid data logging studies have provided usage statistics in different environments.

Using similar data logging studies for CIs, it is possible to get usage statistics of CIs in different environments. In the absence of such studies for CIs, 10 commonly encountered noisy environments reported for hearing aid users have been chosen herein, which include car noise (noise from engine noise at low and high speeds as well as AC noise), office noise (typing, mouse clicking, and occasional copier/printer sound in the background), apartment noise (living room noise with TV on with occasional noise from dishes and AC noise), street noise (moving traffic and wind noise), playground noise (kids screaming, laughing in the background), mall noise (music played in stores, babble noise with reverberation), restaurant noise (babble noise mainly due to music and dishes), train noise (engine noise and the rhythmic noise made by wheels on railing), flight noise (engine noise together with air noise), place of worship noise (people whisper, praying with occasional bell sound in the background). Additional noise can be easily incorporated into the claimed system if needed. It should be pointed out that in response to a noise class which is not present in the noise classes considered, the system selects the class with the closest matching noise characteristics.

System Components:

A. Speech Activity Detector

For extracting noise features, it is required to determine if a captured data frame contains speech+noise or noise-only. After deciding that it is a noise-only frame, noise signal features get extracted and a noise classifier gets activated. In order to determine the presence of noise-only frames, a noise detector based on a voice activity detector (VAD) is used. There are a number of VADs that have been proposed in the literature. Some of the well-known ones include ITU recommended G.729b, SNR-based, zero crossing rate, statistical-based, and HOS-based VADs.

In an embodiment of the claimed invention, the inventors have considered a VAD based on the wavelet packet transform that is already computed as part of our CI speech processing pipeline in order to limit the computational burden on the overall system. In this VAD, the subband power difference is used to distinguish between speech and noise frames. Subband power is computed using wavelet coefficients from the first level WPT coefficients of the input speech frame. Then, the subband power difference (SPD) between the lower frequency band and the higher frequency band is computed as proposed in Equation (1). Next, SPD is weighted as per the signal power, see Equation (2), and the outcome is compressed such that it remains in the same range for different speech segments as indicated in Equation (3). A first order lowpass filter is also used at the end to smooth out fluctuations.

$$SPD(m) = \left| \sum_{n=1}^{N/2} (\psi_{1,m}^0(n))^2 - \sum_{n=1}^{N/2} (\psi_{1,m}^1(n))^2 \right| \quad (1)$$

$$Dw(m) = \quad (2)$$
$$SPD(m)[1/2 + 16/(\log(2))\log(1 + 2\Sigma_i(n=1)^{\uparrow}N \equiv \llbracket y_\perp m(n) \rrbracket$$

$$Dw(m) = SPD(m)\left[\frac{1}{2} + \frac{16}{\log(2)}\log(1 + 2\sum_{n=1}^{N} y_m(n)^2)\right]$$

$$Dc(m) = \frac{1-e^{-2Dw(m)}}{1+e^{-2Dw(m)}} \quad (3)$$

where $\gamma_m$ is the input speech signal of the $m^{tk}$ window with each window containing N samples, $\psi_{1,m}^B(n)$, $\psi_{1,m}^1(n)$ are the wavelet coefficients corresponding to the lower and higher frequency bands at the first level or stage of the decomposition.

To differentiate between noise and speech, a threshold Tv(m) is, set using the adaptive percentile filtering approach, where the smoothed compressed subband power difference Dc is saved in a buffer for 1 s segments as suggested in [19] (i.e., B no. of Dc values from a previous window) and sorted in ascending order (Dcs), see Equation (4). The adaptive threshold is then set as Dcs(b) when the condition in Equation (5) is met. Considering that the noise environment does not change as fast as speech, the threshold value is updated slowly as indicated in Equation (6) with $\alpha_v$=975. A speech or noise decision is made if the Dc(m) value is more than or less than the threshold value Tv(m).

$$Tv(m)=Dcs(b) \quad (4)$$

$$Dcs(b)-Dcs(b-4)>0.008\ Dcs(b)-Dcs(b-4)>0.008 \quad (5)$$

$$\forall b=4\ldots B$$

$$Tv(m)=\alpha_v Tv(m-1)+(1-\alpha_v)Tv(m) \quad (6)$$

Unvoiced segments are generally hard to detect and they are often mistaken as noise frames. Unvoiced frames often occur before or after voiced frames. Hence, the frames which are detected as noise frames just after voiced frames are still treated as speech. In other words, a guard time of 200 ms after voiced segments is considered noting that most consonants do not last longer than 200 ms on average. This reduces the chance of treating unvoiced frames as noise. It should be mentioned that this VAD is not used to update the noise spectrum in the noise suppression component, thus this extra guard time does not harm the noise tracking and it improves the noise classification rate. It is also important to note that this VAD does not depend on any training and it performs well across various SNRs. FIG. 2 shows the noise detector output with and without this guard time when applied to a speech signal recorded at 8 kHz with a male speaker saying the sentences "Glue the sheet to the dark blue background" followed by a 2 s pause and then saying "The birch canoe slid on the smooth planks." FIG. 2C shows the VAD output with the guard time for these speech signals when corrupted by car noise at 5 dB SNR.

B. Noise Features

Various features have been described in the literature for noise characterization. For example, time domain features including zero crossing rate, short time energy, energy entropy, envelope modulation spectra in auditory critical bands have been used, as well as spectral domain features such as spectral roll off, spectral centroid, and harmonicity measure. Noise features derived from LPC and wavelet transforms are also widely used. For this system, various combinations of the above time domain, spectral domain, and MFCC (mel-frequency cepstral coefficients) were examined. Among various feature combinations examined, it was found that the MFCC+ΔMFCC features (26-dimensional feature vector) provided the best compromise between a high classification rate and a low computational complexity allowing the real-time implementation of our smart CI system. Other combinations either did not provide as high classification rates or were computationally intensive and did not allow a real-time throughput to be obtained.

To compute MFCC coefficients, an overlapping triangular filter is applied to the magnitude spectrum of the wavelet packet transform in order to map the magnitude spectrum to mel scale. Here, 40 triangular filters are used, i.e. the 64-frequency bands magnitude spectrum is mapped to 40 bins in mel scale frequency. The lowest frequency considered is 133 Hz, and the first 13 consequent filters are spaced linearly with a bandwidth of 66.66 Hz, the remaining 27 filters are placed such that the bandwidths increase logarithmically with the highest frequency being 4000 Hz. A discrete cosine transform (DCT) is then applied to the logarithm of the magnitude spectrum in mel scale thus generating 13 MFCCs. The first derivatives of MFCCs ΔMFCC are also computed as indicated in Equation (7).

$$\Delta MFCC(m,p)=MFCC(m,p)-MFCC(m-1,p) \quad (7)$$

where MFCC(m, p) represents the $\rho^{tk}$ MFCC coefficient of the $m^{tk}$ window.

C. Environmental Noise Classifier

Different classifiers have been used to classify speech, noise and music classes, or different sound classes. The main classifiers used consist of Neural Network (NN), K-Nearest Neighbor (KNN), Support Vector Machine (SVM), Gaussian Mixture Model (GMM), Hidden Markov Model (HMM). Previous work showed the use of a SVM classifier with radial basis kernel and showed that this classifier provided high classification rates among a number of different classifiers for a two-class noise classification problem. However, the implementation of a SVM classifier is computationally expensive for the multiclass noise classification problem here due to the large number of times feature vectors must be projected. NN, KNN, Bayesian and GMM classifiers were examined and it was found that GMM with two Gaussians generated the best outcome while generating a low computational burden.

Based on training data, a GMM classifier was designed by estimating the Gaussian parameters, i.e. mean, covariance and probability of the Gaussian distributions via K-means clustering and the expectation maximization technique. It should be noted that the GMM classifier training was carried out offline.

D. Noise Suppression

Several environment specific noise suppression algorithms have appeared in the literature. Most of these algorithms are computationally intensive and do not meet the real-time requirement of the claimed invention. For the claimed system, a combination of noise suppression algorithms has been considered. First, the speech and noise variances are estimated by appropriately weighting the received signal variance. This weighting is a function of the prior and posterior SNRs and is derived using a data driven approach by selecting a gain parameter previously stored in a lookup table.

An important aspect in speech enhancement is to accurately track noise so that it is not overestimated or underestimated. Overestimation leads to removal of speech in the enhanced speech signal leaving the speech distorted and unintelligible, and underestimation leads to generation of a noise. There are several methods for tracking the noise spectrum. In general, these methods attempt to update the noise spectrum using the received signal spectrum with a greater amount of confidence when the probability of speech presence goes low. The deployment of the data-driven approach for noise tracking originally proposed by Erkelens et al. (2007) and Erkelens and Heusdens (2008) is further discussed below. It should be noted that other tunable noise suppression algorithms can be used in our system provided that they can be run in real-time.

Considering an additive noise scenario, Equation (8) sets forth clean, noise and noisy received signals represented by $x_m(n)$, $d_m(n)$ and $y_m(n)$ and $y_m(n)$, respectively, where m denotes the window number. The equivalent short-time DFT is given in Equation (9) where k represents the frequency bin of FFT. The priori and posterior SNRs for the speech spectral estimation are stated in Equation (10). Equations (8) (9) (10) define the parameters used to model an additive noise system, and the classical definitions of priori and posteriori SNRs.

$$y_m(n) = x_m(n) \tag{8}$$

$$Y_m(k) = x_m(k) + D_m(k) \tag{9}$$

$$\xi_m(k) = \frac{\lambda_x(k)}{\lambda_d(k)}, \; \gamma_m(k) = \frac{Y_m^2(k)}{\lambda_d(k)} \tag{10}$$

where $\xi_m(k)$ denotes the prior SNR, $Y_m(k)$ the posterior SNR at the frequency bin k, $\lambda_d$ the noise variance and $\lambda_x$ the clean speech variance. The prior SNR and posterior SNR for the speech spectral estimation are obtained by using the decision directed approach as specified by Equations (11) and (12) for noise suppression.

$$\widetilde{\xi_m}(k) = \alpha_{dd} \frac{\widetilde{X_{m-1}^2}(k)}{\widetilde{\lambda_d}(k)} + (1 - \alpha_{dd})\max\left(\frac{\widetilde{Y_m^2}(k)}{\widetilde{\lambda_d}(k)} - 1, \xi_{min}\right) \tag{11}$$

$$\widehat{\gamma_m}(k) = \frac{\widetilde{Y_m^2}(k)}{\widetilde{\lambda_d}(k)} \tag{12}$$

where $\alpha_{dd}$ is a smoothing parameter which depends on the speech probability, and $\xi_{min}$ is a small number greater than 0. The use of the non-ideal prior SNR estimate which is derived using the previous window speech spectral estimation leads to erroneous spectral estimates. This error is fed back to the system. To avoid this error, a prior SNR estimate, $\widetilde{\xi_{NT\,m}}$ based on the previous window spectra is used as shown in Equation (13).

$$\widetilde{\xi_{NT\,m}}(k) = \alpha_{NT} \frac{Y_{m-1}^2(k)}{\widetilde{\lambda_d}(k)} + (1 - \alpha_{NT})\max\left(\frac{Y_m^2(k)}{\widetilde{\lambda_d}(k)} - 1, \xi_{min}\right) \tag{13}$$

The noise variance and speech spectra are then obtained according to the weighted received signal spectra specified in Equations (14) and (15), where the weight is a function of the prior and posterior SNR estimates.

$$\widetilde{\lambda_d}(k) = G_D(\widetilde{\xi_{NT\,m}}(k), \widehat{\gamma_m}(k)) Y_m^2(k) \tag{14}$$

$$\widetilde{X_m^2}(k) = G_x(\widetilde{\xi_m}(k)) \widehat{\gamma_m}(k) \tag{15}$$

$G_D$ is derived using the data driven approach, and $G_x$ is derived using the logMMSE estimator as indicated in Equation (16).

$$G_x(\widetilde{\xi_m}(k), \widehat{\gamma_m}(k)) = \frac{\widetilde{\xi_m}(k)}{\widetilde{\xi_m}(k) + 1} \exp\left\{\int_{vx}^{\infty} \frac{e^{-t}}{t} dt\right\} \tag{16}$$

where $$vx = \frac{\widetilde{\xi_m}(k) * \widehat{\gamma_m}(k)}{\widehat{\gamma_m}(k) + 1}.$$

Figure 3:
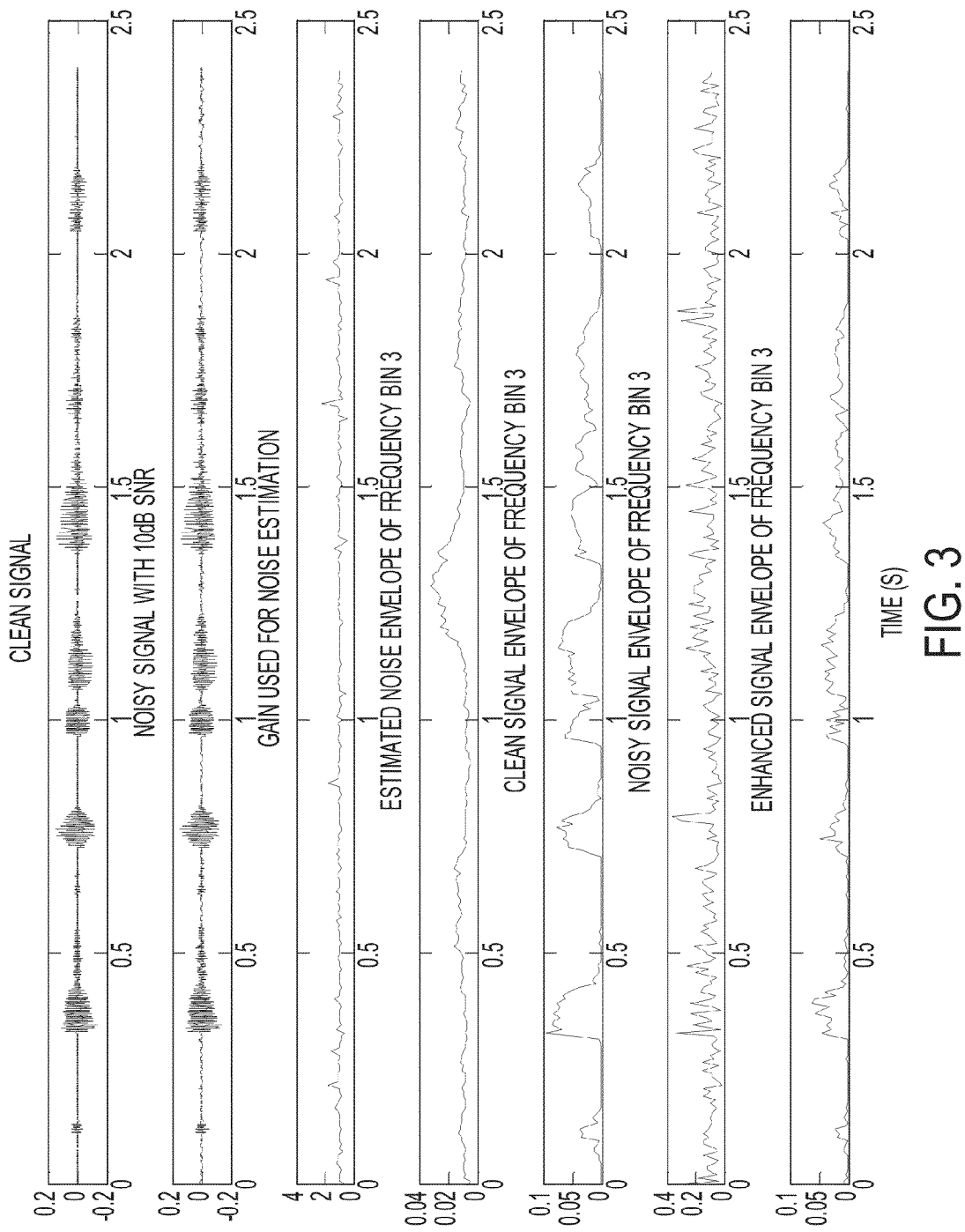
FIG. 3 illustrates plots showing clean speech signal, noisy speech signal corrupted by car noise at 10 dB, gain used during noise estimation, estimated noise envelope, clean signal envelope, noisy signal envelope, enhanced signal envelope of frequency bin 3 in accordance with some embodiments of the invention.

A gain table is thus derived during training for each noise class for the prior SNR from −20 to 40 dB and for the posterior SNR from −30 to 40 dB. In other words, the $G_D$ lookup table that is used for tuning becomes of size 61×71 for each noise class. To illustrate the working of the noise tracking algorithm, FIG. 3 shows the clean speech, the noisy speech corrupted by car noise, the selected gain function G_D for frequency band 3 and the enhanced speech.

The classical PESQ (perceptual evaluation of speech quality) and LLR (log-likelihood ratio), are considered to examine the system performance in the next section. In addition, the three measures which highly correlate with subjective speech quality are also examined. These measures consist of signal distortion (Csig), background distortion (Cbak) and overall quality (Covl).

In an embodiment of the invention, the system is implemented on a PC and a PDA platform. The PDA platform has limited computational and memory resources as compared to the PC platform and has been used as a research platform for cochlear implants. The PDA platform has been recently approved by FDA for clinical trials. As mentioned earlier, the input speech frame was windowed into 11.6 ms windows which corresponded to 128 sample windows. The overlap between windows for computing the recursive WPT was decided depending on the required stimulation rate. The detail and analysis coefficients from the first stage of WPT were used in the noise detector component. The MFCC features were computed for every alternate noise-only window using the WPT coefficients at the 6th stage to achieve real-time performance. The MFCC feature vector after normalization was used as the input feature vector to the trained GMM classifier.

The decision made by the GMM classifier for 20 consecutive noise frames was used to generate a class decision. The majority voting between 20 decisions of classifier was used because of the non-perfect behavior of the noise detector as some of the voiced sections would get labeled as noise. The number of windows was chosen to be 20. A further increase in the number of windows did not show much improvement in the performance. Frequent unnecessary switching from one noise class to another produces unpleasant distortions. As an example, suppose at restaurant, someone slams a door, which may be regarded as some other noise other than restaurant background. Since the door slam noise is not a sustained type of noise, changing the noisy environment from restaurant to some other and then going back to restaurant noise is unnecessary. Hence, a median filter with a duration of 2 s was used to eliminate such frequent switching. As a result, a switch was only made when the noise environment was sustained for more than 2 s. Of course, this duration depends on user comfort and can be easily changed in the system for any lesser or longer duration.

In an embodiment of the invention, the system implementation was done in C and an interactive GUI was added using LabVIEW. The PC platform used for implementation had a processor clock rate of 3.33 GHz with 4 GB RAM, and the PDA platform had of a processor clock rate of 624 MHz with 512 MB RAM.

Due to the limited computing and memory resources of the PDA platform, several code optimizations are required in order to achieve a real-time throughput. The rate at which the classifier is activated is reduced by every alternate noise frame. Since the PDA processor is a fixed-point processor, the implementation is done using fixed-point integer arithmetic. Parts of the code, where the accuracy is crucial and a large dynamic range is required, are implemented using 32 bit variables while the other parts are implemented using 16 bit variables to save processing time. In addition, the exponential integral is implemented as a lookup table, and the lookup table is designed in such a way that the size of the table was minimized at the expense of negligible loss in accuracy. Different sections of the table are created with different resolutions to save memory and are arranged in a tree structure to speed up the lookup table search.

In an embodiment of the invention, 100 sentences of approximately 3 s duration each were used to serve as the speech material along with 10 noise classes with 5 min recording for each class. Both noise and speech are sampled at 8 kHz. All the speech sentences are concatenated to form speech segments of 30 s duration with is pause between them. A pause is deliberately added between sentences so that the noise classification decision is made based on the noise present during speech pauses. 50% of the data were randomly selected and used for training and the remaining 50% for testing. Noise added to the speech sentences is randomly changed after every 30 s. Table 1 shows the classification rates of the noise adaptive CI system in accordance with an embodiment of the invention, averaged over 10 noise classes at different SNRs.

TABLE 1

| SNR (dB) | Classification rate (%) |
|---|---|
| 0 | 97.1 |
| 5 | 96.8 |
| 10 | 96.2 |
| 15 | 96 |

Figure 4:
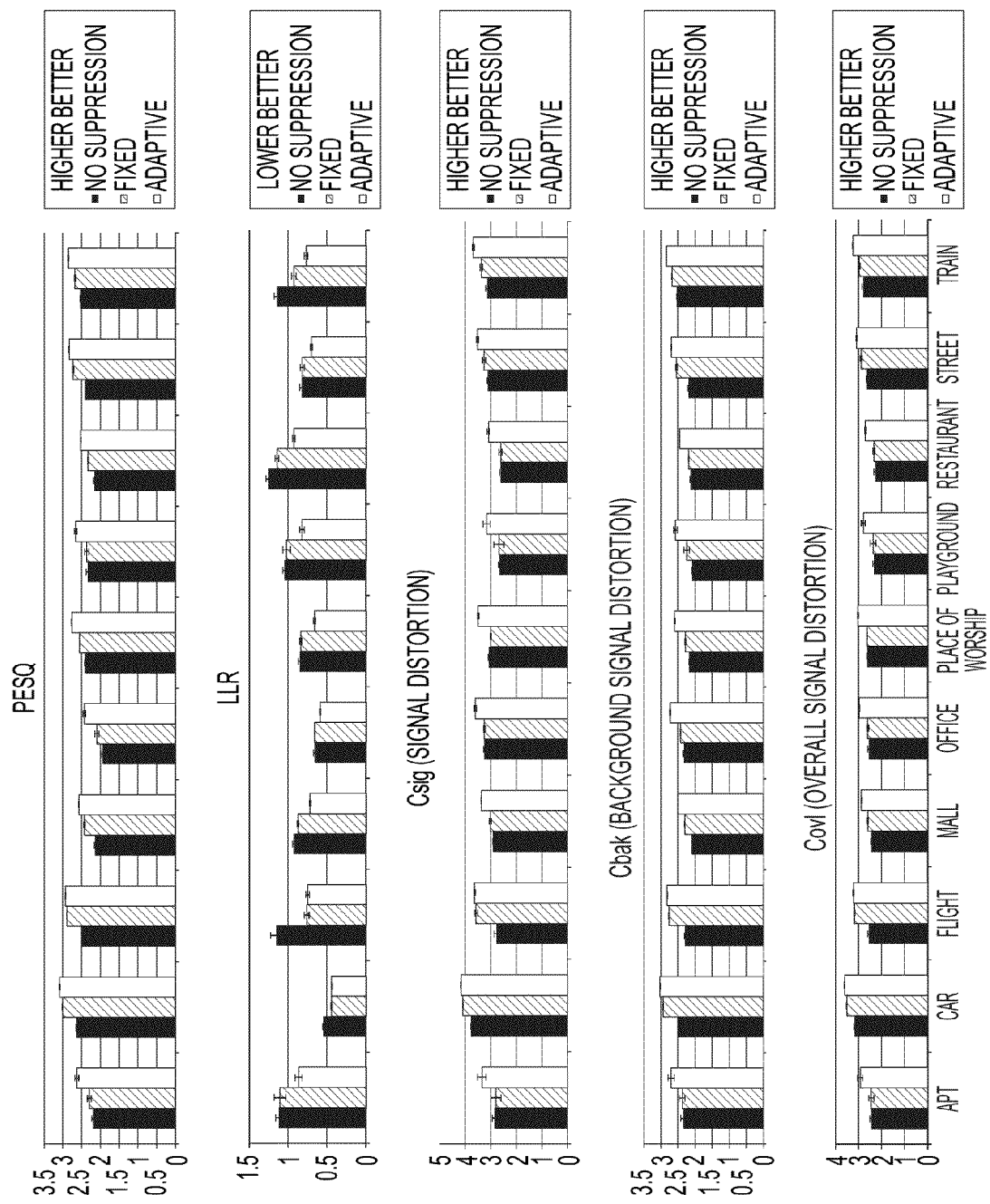
FIG. 4 illustrates bar graphs showing the performance of five speech enhancement measures for smart adaptive noise suppression system, fixed noise suppression system and no noise suppression system in terms of the objective measures PESQ, LLR, Csig, Cbak and Covl, in accordance with some embodiments of the invention.
Figure 5A:
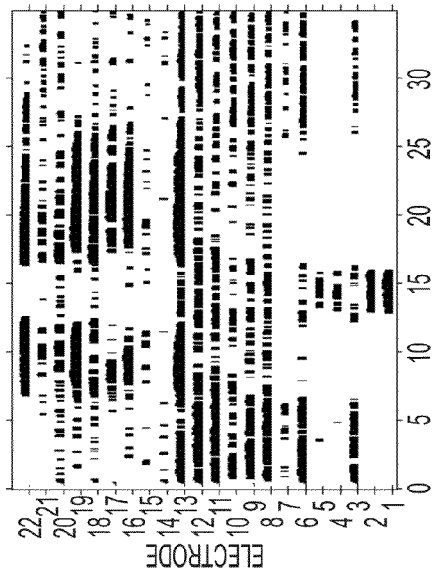
FIG. 5 illustrates electrodograms of the utterance 'asa': (a) clean signal; (b) noisy signal with street noise at 5 dB SNR; (c) after adaptive noise suppression; and (d) after fixed noise suppression.
Figure 5B:
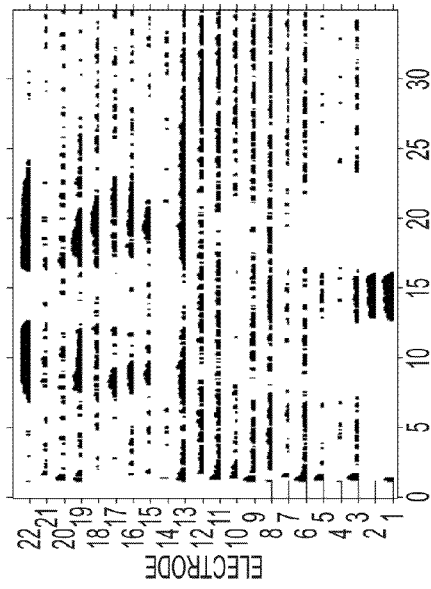
Figure 5C:
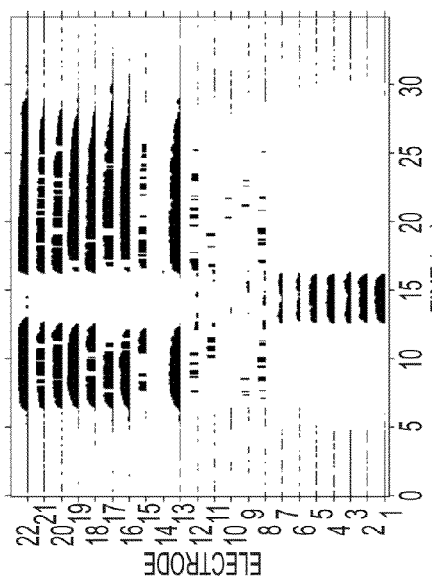
Figure 5D:
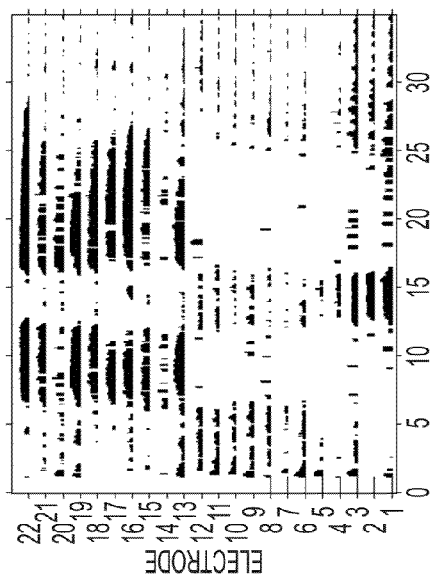

In an embodiment of the invention, the performance of the adaptive noise suppression approach was studies by comparing it against two other scenarios: one without any speech enhancement or noise suppression and the other with a fixed (non-environment specific) noise suppression algorithm. The comparison was done in terms of the following objective measures: PESQ, LLR, Csig, Cbak, and Covl. The comparative results are shown in FIG. 4. This figure shows the data for the 5-dB SNR conditions—similar improvements were observed for the other SNR conditions. As can be seen from this figure, the adaptive noise suppression approach provided better performance across the above measures as compared to the no-noise suppression and fixed-noise suppression systems. For the playground environment, for instance, the PESQ improved from 2.3 with the fixed-noise suppression system to 2.6 with the adaptive system.

For further illustration, FIG. 5 shows electrodograms, derived using an 8-of-22 stimulation strategy, for the speech segment 'asa' spoken by a female talker. More specifically, this figure shows the electrodogram of clean speech, noisy speech with street noise added at 5 dB SNR, and enhanced electrodogram with the adaptive and fixed noise suppression algorithms. It is clear from this figure that the adaptive system is more effective in suppressing noise than the fixed-suppression system. It is worth mentioning that although following a misclassification a different gain parameter than the one corresponding to the correct noise class might be selected, it was found that the performance of the system still improved compared to the no-noise suppression system.

Table 2 shows the real-time profiling of the system components on both the PC and PDA (smartphone) platforms. The Table lists the times required for the specified components in the system to process 11.6 ms frames corresponding to 128 samples at 22,050 Hz sampling rate. As indicated in the table, the PDA platform took a much higher processing time than the PC platform for processing 11.6 ms frames due to its limited processing power. However, it still achieved a real-time throughput by processing 11.6 ms frames in about 8.5 ms.

TABLE 2

| | Total Time in ms | Recursive WPT | Speech activity detector | Feature extraction, classifier | Noise suppression | Channel envelope computation |
|---|---|---|---|---|---|---|
| PDA | 8.41 | 1.24 | 0.91 | 2.03 | 2.40 | 1.83 |
| PC | 0.70 | 0.12 | 0.03 | 0.14 | 0.36 | 0.05 |

An embodiment of the claimed invention is directed to a real-time noise classification and tuning system for cochlear implant applications. The system is capable of automatically selecting the optimized parameters of a noise suppression algorithm in response to different noisy environments. The feature vector and the classifier deployed in the system to automatically identify the background noise environment are carefully selected so that the computation burden is kept low to achieve a real-time throughput. The results reported herein indicate improvement in speech enhancement when using this intelligent real-time cochlear implant system.

It will be appreciated that the above description for clarity has described embodiments of the invention with reference to different functional units and processors. However, it will be apparent that any suitable distribution of functionality between different functional units or processors may be used without detracting from the invention. For example, functionality illustrated to be performed by separate processors or controllers may be performed by the same processor or controllers. Hence, references to specific functional units are only to be seen as references to suitable means for providing the described functionality rather than indicative of a strict logical or physical structure or organization.

The invention can be implemented in any suitable form including hardware, software, firmware or any combination of these. The invention may optionally be implemented at least partly as computer software running on one or more data processors and/or digital signal processors. The elements and components of an embodiment of the invention may be physically, functionally and logically implemented in any suitable way. Indeed the functionality may be implemented in a single unit, in a plurality of units or as part of other functional units. As such, the invention may be implemented in a single unit or may be physically and functionally distributed between different units and processors.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term comprising does not exclude the presence of other elements or steps.

Furthermore, although individually listed, a plurality of means, elements or method steps may be implemented by e.g. a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category but rather indicates that the feature is equally applicable to other claim categories as appropriate. Furthermore, the order of features in the claims do not imply any specific order in which the features must be worked and in particular the order of individual steps in a method claim does not imply that the steps must be performed if this order. Rather, the steps may be performed in any suitable order. In addition, singular references do not exclude a plurality. Thus references to "a", "an", "first", "second" etc do not preclude a plurality.

What is claimed is:

1. An audio device system comprising an audio device and a control device,
   the control device comprising: a signal interface that is adapted to receive data representing the acoustic environment external to the ear, and transmit parameters of a noise suppression algorithm to the audio device; and a module for analyzing the data representing the acoustic environment external to the ear, and calculating the noise suppression algorithm for digital signal processing, the control device being operable to be responsive to the acoustic environment data transmitted thereto to automatically select optimized parameters of the noise suppression algorithm based upon the data and to transmit the algorithm parameters to the audio device, wherein instructions executed by the control device, and which enable the control device to perform the audiometric process in cooperation with the audio device, are stored within the control device;
   wherein the audio device is adapted to receive the algorithm parameters transmitted thereto by the control device and to perform speech enhancement automatically in real time using the received algorithm parameters without user intervention, and wherein the audio device is a cochlear implant.

2. The audio device system according to claim 1 further comprising a computer in communication with the control device for at least one of signal analysis, algorithm processing, and audiometric examination.

3. The audio device system in accordance with claim 1, wherein the system is implemented on a smartphone platform.

4. The audio device system of claim 1 further comprising a feature vector and a classifier.

5. A method of operating an audio device, the method comprising: providing an audio device and a control device, the control device comprising a signal interface that is adapted to receive data representing the acoustic environment external to the ear, and transmit parameters of a noise suppression algorithm to the audio device, and wherein the audio device is a cochlear implant; and a module for analyzing the data representing the acoustic environment external to the ear, and calculating the noise suppression algorithm for digital signal processing, the control device being operable to be responsive to the acoustic environment data transmitted thereto to automatically derive the noise suppression algorithm parameters based upon the data and to transmit the noise suppression algorithm parameters to the audio device; wherein the audio device is adapted to receive the noise suppression algorithm parameters transmitted thereto by the control device and to perform speech enhancement in real time using the received noise suppression algorithm, wherein instructions executed by the control device, and which enable the control device to perform the audiometric process in cooperation with the audio device, are stored within the control device; the method further comprising the steps of:
   adjusting the audio device in an audiometric process to adapt the audio device to the hearing loss of the user;
   deriving data representing the acoustic environment external to the ear;
   transmitting the data representing the acoustic environment external to the ear to the control device;
   analyzing the data representing the acoustic environment external to the ear and automatically selecting optimized parameters of the noise suppression algorithm for performing speech enhancement automatically in real time;
   transmitting the noise suppression algorithm parameters to the audio device; and
   performing speech enhancement using the received noise suppression algorithm parameters without user intervention.

6. The method according to claim 5 and further comprising providing a computer in communication with the control device for at least one of signal analysis, algorithm processing, and audiometric examination.

* * * * *